(12) United States Patent
Nóbrega et al.

(10) Patent No.: US 9,597,162 B2
(45) Date of Patent: Mar. 21, 2017

(54) VIBRATING ORTHODONTIC DEVICE

(71) Applicants: Celestino José Prudente Nóbrega, Pindamonhangaba (BR); Rogerio Amaral Tupinambá, Pindamonhangaba (BR); Gustavo Ravanhani Matuck, Sao Jose dos Campos (BR); Jorge Luis Guedes Alves, Sao Jose dos Campos (BR)

(72) Inventors: Celestino José Prudente Nóbrega, Pindamonhangaba (BR); Rogerio Amaral Tupinambá, Pindamonhangaba (BR); Gustavo Ravanhani Matuck, Sao Jose dos Campos (BR); Jorge Luis Guedes Alves, Sao Jose dos Campos (BR)

( * ) Notice: Subject to any disclaimer, the term of this patent is extended or adjusted under 35 U.S.C. 154(b) by 428 days.

(21) Appl. No.: 14/152,294

(22) Filed: Jan. 10, 2014

(65) Prior Publication Data

US 2015/0064640 A1 Mar. 5, 2015

(30) Foreign Application Priority Data

Aug. 28, 2013 (BR) .......................... 20 2013 022037

(51) Int. Cl.
| | | |
|---|---|---|
| *A61C 7/00* | (2006.01) | |
| *A61B 5/01* | (2006.01) | |
| *A61B 5/145* | (2006.01) | |
| *A61B 5/00* | (2006.01) | |

(52) U.S. Cl.
CPC ................ *A61C 7/008* (2013.01); *A61B 5/01* (2013.01); *A61B 5/14507* (2013.01); *A61B 5/14539* (2013.01); *A61B 5/682* (2013.01)

(58) Field of Classification Search
CPC ........... A61C 7/00; A61C 7/002; A61C 7/008; A61C 7/02; A61C 7/023; A61C 7/026; A61C 7/04; A61C 7/06; A61C 7/065; A61C 7/08; A61C 7/10; A61C 7/12; A61C 7/125; A61C 7/14; A61C 7/141; A61C 7/143; A61C 7/145; A61C 7/146; A61C 7/148; A61C 7/18; A61C 7/20; A61C 7/28; A61C 7/287; A61C 7/303; A61B 5/01; A61B 5/14507
USPC ............................................... 433/2, 3, 6–24
See application file for complete search history.

(56) References Cited

U.S. PATENT DOCUMENTS

| | | | |
|---|---|---|---|
| 2006/0234189 A1* | 10/2006 | Duret .................. | A61C 19/066 433/215 |
| 2007/0009856 A1* | 1/2007 | Jones .................... | A61C 17/20 433/215 |
| 2008/0233541 A1* | 9/2008 | De Vreese ........... | A61C 19/066 433/216 |
| 2011/0007920 A1 | 1/2011 | Abolfathi et al. | |
| 2012/0040300 A1 | 2/2012 | Levens et al. | |
| 2012/0322018 A1 | 12/2012 | Lowe et al. | |
| 2014/0335467 A1* | 11/2014 | Yamamoto ............. | A61C 7/008 433/6 |

* cited by examiner

*Primary Examiner* — Yogesh Patel
(74) *Attorney, Agent, or Firm* — McKee, Voorhees & Sease, PLC

(57) ABSTRACT

The present invention relates to a vibrating orthodontic device (1) to be used as an adjuvant for the treatment of correcting malocclusions, the capture comprising vibrating devices (5 and 6) that promote teeth vibration, improving movement of teeth, reducing pain and the time of treatment.

12 Claims, 3 Drawing Sheets

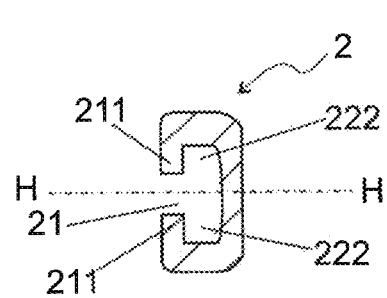
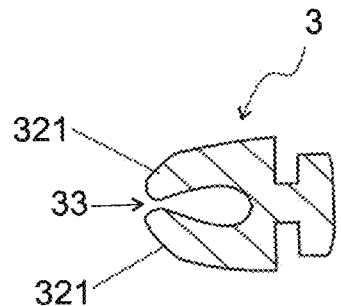
FIG. 6    FIG. 7
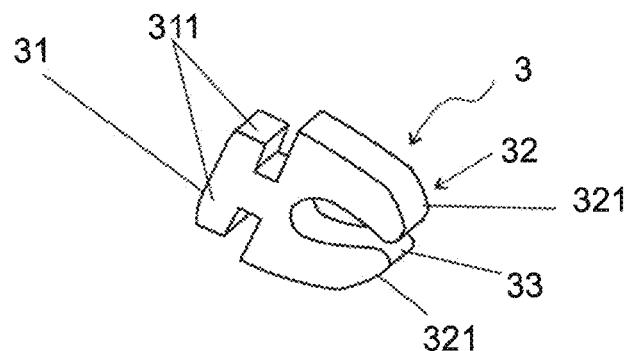
FIG. 8
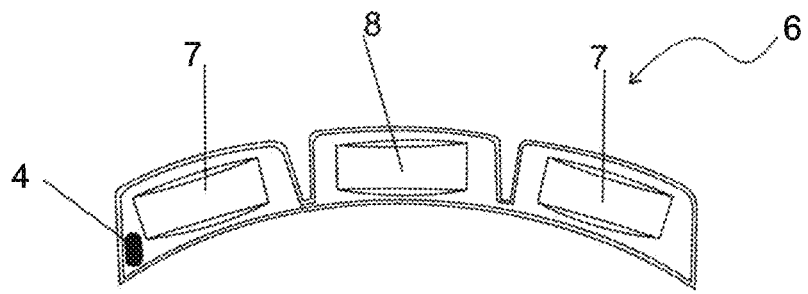
FIG. 9

VIBRATING ORTHODONTIC DEVICE

The present invention relates to a vibrating orthodontic device used to aid the treatment comprising correcting malocclusions.

PRIOR ART

The person skilled in the art is aware of the importance of correct dental positioning, which aims the appropriate function and aesthetics for each individual. In an orthodontic treatment, light forces are applied to teeth by means of specific apparatus, that is, the orthodontic device.

The duration of treatment depends on several factors, such as the biological response of the patient, the amount of force applied, the time length that the forces act, the complexity of the case and patient's cooperation, among others.

A corrective orthodontic treatment has an average duration of 18 to 30 months, depending whether dental extractions are needed or not, which tend to extend the course of treatment.

The following are among the most common complaints of patients undergoing orthodontic treatment: discomfort by the presence of the device; painful sensitivity from the inflammatory reaction associated with teeth movement; and treatment duration.

Several studies have been made to reduce such complaints, reducing discomfort and accelerating dental movement through the application of pulsating forces. It is known that the analgesic effect of vibratory stimulation is more effective than aspirin for pain relief by orthodontic movement. A relief of pain due to other types of dental problems, such as pulpitis and post-operative pain was further verified.

In addition to these advantages, teeth movement is significantly higher when using vibratory stimulation, and despite the large increase of teeth movement speed, there is no kind of damage to the teeth support tissue or to the bone tissue.

Thus, devices have been developed that apply vibration effect on teeth, associated with the orthodontic apparatus aiming at pain and treatment time reduction.

US patent documents US20120040300 and US20120322018 can be cited among the prior art documents which relate to the subject matter. They relate to a fork shaped device adapted to the teeth by occlusion (bite) which has the function of producing a vibrating effect, transmitting to the fork, and gathering data related to the frequency of use and patient cooperation. There is also another apparatus intended to transmit the gathered data and recharge the battery of the vibrating device.

The US patent application US20110007920 discloses a vibrating device comprising an electronic device and a transducer that is coupled to the molar for directing the vibratory stimulus to the teeth. It is possible to choose, with this device, which teeth will receive the stimulus, individually or together.

These devices disclosed in these documents have as a main disadvantage their high costs due to the great complexity in the development and data type provided by such devices. Their costs reach 30% of the total value of a simple orthodontic treatment. It is a device with many features, but also very expensive.

In the case of external devices, there is little patient's cooperation, since they are bulky and uncomfortable. They also present drawbacks such as external wires or even splints for neck support, which are quite unattractive.

Yet another disadvantage is the difficulty of adopting a protocol so that only specific parts of the arch are stimulated which, although only the device disclosed in US20110007920 present such possibility, its design internally invades the oral cavity occupying the space of the tongue, which is quite uncomfortable, and for this reason its acceptance by patients is reduced.

Another factor of discouragement of using these devices is the need of stabilization in the oral cavity by biting, since in vibration protocols requires keeping the apparatus in contact with teeth for several minutes, patients tend to report muscle fatigue by maintaining the stabilization force for too long.

The present invention was developed in order to solve the prior art problems, it relates to a vibrating orthodontic device to be used associated with orthodontic appliances for correcting malocclusions.

The present device presents a very simple design and acts only as a vibrating device, without sophisticated features, thus having a greatly reduced cost in comparison with the previous art apparatuses.

Another advantage of this device is its reduced size and the fact of dispensing the use of any type of extra oral accessory for fixation and stabilization, which facilitates the issue of patient collaboration.

This device comprises independent segments which makes the applicability of activation protocols by isolated arch segments very simple, and also allows the activation of all segments simultaneously.

The apparatus can be used associated with orthodontic appliances fixed to the external or internal surface (vestibular) of teeth, where in the first embodiment it eliminates the need for stabilization by patient's bite, since the apparatus has sliding clips that attach directly to the arch of an orthodontic appliance, thereby reducing patient fatigue and increasing their cooperation index.

One of the great challenges of creating a device of this type resides in the difficulty of associating a simplified and small design with ease of use, patient cooperation and vibrating effectiveness.

By integrating the strap design with the vibrating devices by segments, it was possible to provide versatility to the device, since the sliding clips, attached to the orthodontic appliance, transmit forces directly to it, without the need of gripping by bite, which only larger volume devices, that are much more complex and expensive, partially offer.

Another advantage of the present device is the manner by which the clips slide along the vibrating strap, allowing their adaptation to any type of vestibular orthodontic appliance, regardless of the type of malocclusion or of spaces present between the brackets, in the upper or lower arch.

Moreover, it is possible to replace the clips as needed, as well as to use as many clips as needed for a better device fixation. The clips may also be replaced by bite plates that are also fixed to the strap and are recommended to users of lingual orthodontic appliances.

Schematic drawings of the vibrating orthodontic device are presented below, whose dimensions and ratios are not necessarily the real scale, since the figures have the only purpose of presenting, in a didactic manner, the various aspects of this invention, whose scope of protection is solely set forth by the scope of the appended claims.

FIG. 6 illustrates a cross-section magnified view along the line D-D shown in FIG. 1.

FIG. 7 illustrates a cross-section magnified view of the fastening clip (3).

FIG. 8 illustrates a perspective view of the fastening clip (3).

FIG. 9 illustrates a cross-section magnified view of the frontal vibrating device (6).

DESCRIPTION OF THE ILLUSTRATED EMBODIMENTS

Figure 1:
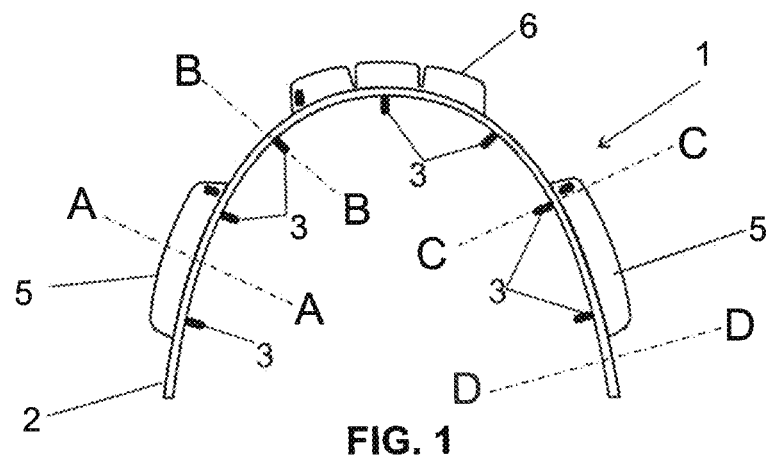
FIG. 1 illustrates a top view of the vibrating orthodontic device (1) of the present innovation.

As illustrated in the attached drawings, the present invention relates to a vibrating orthodontic device comprised by vibrating devices (5 and 6) arranged in a vibrating strap (2) and a plurality of clips (3) coupled to said strap in a sliding manner.

Said vibrating devices (5 and 6), preferably in member of three, are equally spaced on the strap (2), one on the front (6) and two on the back (5) positioned next to the end of the strap, on the right and left of the dental arch. The frontal device (6) is slightly different from the back devices (5) since it presents frontal slits that partially divide it into three segments (FIGS. 1, 2, 9, 10 and 11), while the back devices (5) have a single body (FIGS. 1, 2, 10 and 11).

The vibrating devices (5 and 6) comprise at least one battery (7), a micro vibrator (8) and an actuating element (4), all connected together in order to enable the device (5 and 6) as a whole to vibrate when turned on by the switch (4).

The actuating element (4) is anyone suitable to the type of device (5 and 6), such as a switch or a remote actuating component that can receive any type of actuating signal, such as rays of light, infrared radiation, radio waves, ultrasound, etc. The type of transmitting device is thus chosen according to the mode of transmission, and can be a simple remote control, a smartphone, etc.

The vibration frequency, as well as the type of use of the vibrating appliance (1) are configurable according to the micro vibrator (8) and batteries (7) chosen. Preferably, the vibrating devices (5 and 6) are wrapped by plastic material that, besides allowing a slight deformation, seal the internal components, isolating them from the oral fluids.

Figure 3:
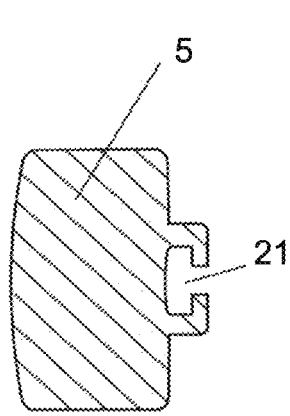
FIG. 3 illustrates a cross-section magnified view along the line A-A shown in FIG. 1.
Figure 4:
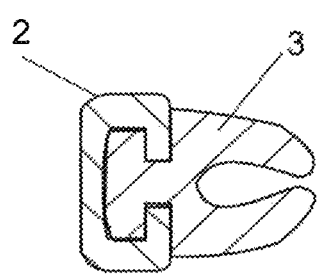
FIG. 4 illustrates a cross-section magnified view along the line B-B shown in FIG. 1.
Figure 5:
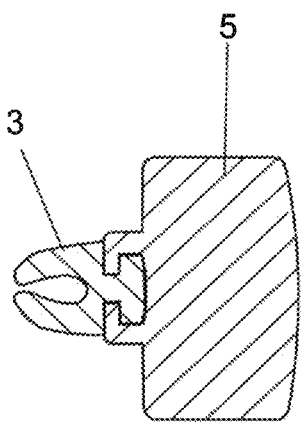
FIG. 5 illustrates a cross-section magnified view along the line C-C shown in FIG. 1.
Figure 13:
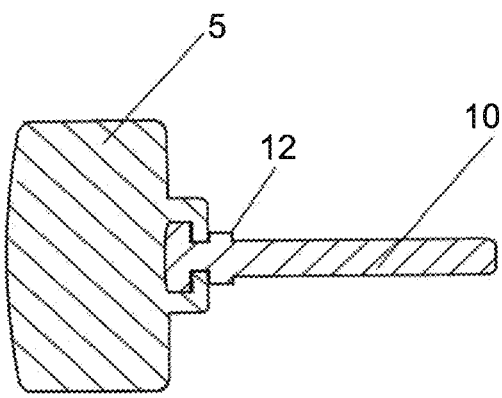
FIG. 13 illustrates a cross-sectional magnified view along the line F-F shown in FIG. 10.

The vibrating strap (2) is preferably comprised by the same plastic material and it is attached to the vibratory devices (5 and 6), as illustrated in FIGS. 3, 5 and 13.

Said strap (2) has its external surface coupled to the vibrating devices (5 and 6) and its internal surface, faced the dental arch, is provided with a track (21) where the clips (3) are coupled in a sliding manner.

The track (21) is in a "C" shaped cross-section with longitudinal tabs (211) towards the central transversal axis (H-H) in order to provide two housings (222), where part of the clips (3) are housed.

The clips (3) comprise a coupling end (31) on the track (21), which is provided with upper and lower wing (311) that retain the clips (3) within the housings (222) of the track (21), allowing them to slide, but preventing them from detaching from the strap (2) due to the wings (311) that are retained by the tabs (211) of the track (21). The opposite end (32) of the clip (3) comprises a slit (33) that enlarges when advancing towards the coupling end (31), forming a cross-section opening similar to a drop form. Such slit (33) divides the end (32) of the clip (3) into two tabs (321), forming a kind of clamp. By engaging the clip (3) in to an arch (91) of an orthodontic appliance (9), the tabs (321) separate allowing the passage of the arch (91), which is then housed in the enlarged portion of the slit (33), retaining the vibrating device (1) in the orthodontic appliance (9). Thus, the clip (3) surrounds the arch (91) on the widest portion of the slit (33). The arch (91) is only released when applying a counterforce for withdrawing the clip (3).

Figure 2:
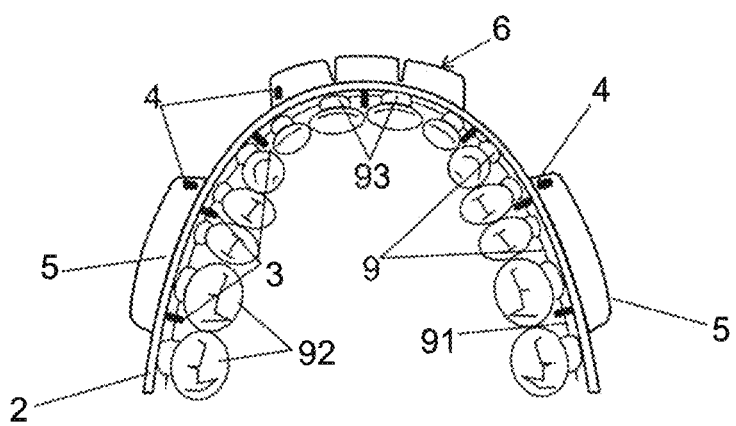
FIG. 2 illustrates a top view of the vibrating orthodontic device (1) fixed to a conventional orthodontic appliance (vestibular).

Said strap (2) extends along the length of the orthodontic appliance (9), and the vibrating orthodontic device (1) can then be connected to the appliance (9) by means of the clips (3) that are moved along the strap (2) until the best suited position to be coupled to the arch (91) (see FIG. 2). For example, in the free space between two consecutive brackets (93). Since the clip (3) is free to slide on the track (21), as many clips (3) as deemed necessary can be used to perform a perfect adaptation of the vibratory device (1) to the arch (91), and this to the orthodontic appliance (9).

The clip design (3) (see FIGS. 4, 5, 7 and 8) favors its adaptation to any arch or orthodontic wire type and gauge (91), especially its slit (33) that, being drop-shaped (FIG. 8), it provides versatility to the clip (3), granting clamp properties to it.

In order to allow an adaptation of the present vibrating orthodontic device (1) in patients with inner orthodontic appliance (lingual) (FIG. 11) or to devices that prevent its attachment on the external arch by means of clips (3), there are bite plates (10 and 11) (see FIGS. 10 and 11) integrated with the clips (12) that, in this particular embodiment, it do not have slit ends, thus being integrated with the bite plates (10 and 11) so as to allow their coupling to the track (21) of the same sliding form.

In this constructive variant, the vibrating stimulus from the device (1) is transmitted to the teeth (92) and then, to the dental support structures (periodontal ligaments and bones), where the dental movement processes occur.

Preferably, the bite plates (10, 11) have two different sizes, one minor bite plate (11), to be used in the front portion of the strap (2), and a larger bite plate (10) in the back portion of the strap (2), both with fastening clips (12) that hold them to the strap (2), and which allow movement along the entire length of strap (2). Said bite plates (10, 11) are made of thermoplastic material, what advantageously allows their conformation according to the patient's bite, before being used.

Each front bite plate (11) is coupled to the strap (2) by at least two fastening clips (12) that can be moved along the strap (2). This plate (11) preferably has constant thickness and it is thicker than the back plate (10), which enables the perfect adaptation of the bite on both plates (10 and 11) at the same time.

Figure 10:
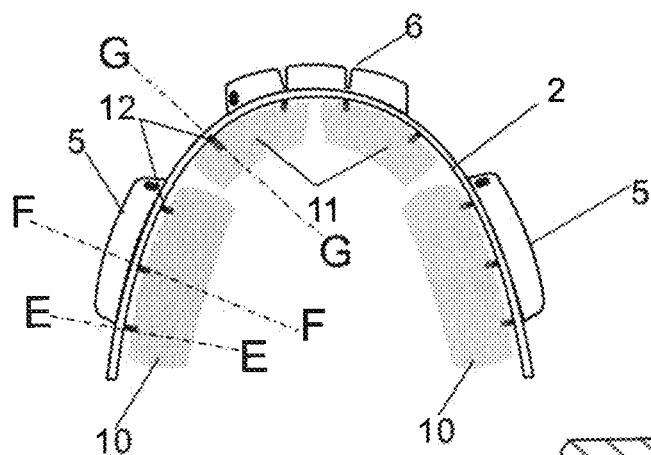
FIG. 10 illustrates a top view of a second embodiment of the vibrating orthodontic device (1) of the present innovation.
Figure 11:
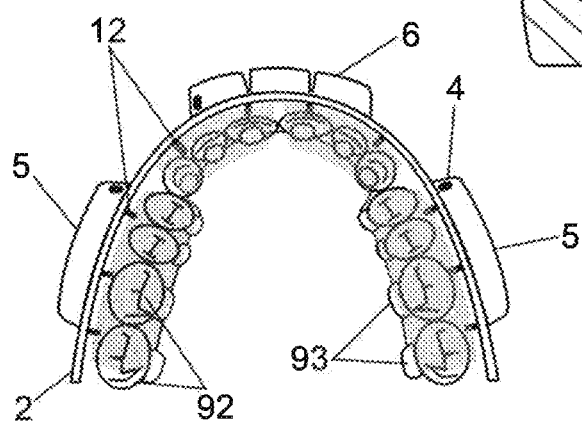
FIG. 11 illustrates a top view of the second embodiment of the vibrating orthodontic device (1) applied to an inner orthodontic appliance (lingual).
Figure 14:
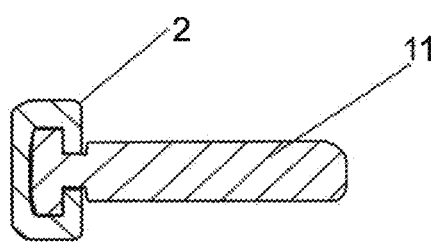
FIG. 14 illustrates a cross-sectional magnified view along the line G-G shown in FIG. 10.

The back bite plate (10) is coupled to the strap (2), as shown in FIGS. 10 and 11, by three fastening clips (12) that can be moved along the vibrating strap (2). The clips (12) comprise one coupling end (121) to the track (21) equipped with upper and lower wings (122) that retain the clips (12) within the housings (222), on the opposite end (123) of the clip (12) there are bite plates (10 and 11) that are integrated with clips (12).

Figure 12:
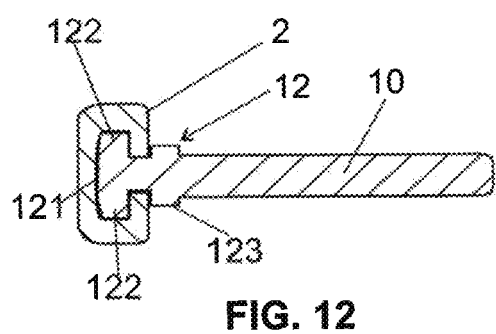
FIG. 12 illustrates a cross-sectional magnified view along the E-E line shown in FIG. 10.

Preferably, the back bite plates (10) have variable thickness, being thinner on their back portion (FIG. 12) than on their front portion (FIG. 13), thus ensuring a more precise adaptation to the teeth when biting the plate (10).

Whatever the type of orthodontic appliance (vestibular or lingual), the vibrating devices (5 and 6) are connected to the strap (2) or retained by occlusion in order to allow transmission of the stimulus to the apparatus (9)/teeth (92), whether through fastening clips (3) or bite plates (10, 11).

Then, for adjusting the vibrating device in patients with conventional orthodontic appliance (vestibular) the fastening clip (3) must be used (as illustrated in FIG. 2) and, for lingual orthodontic appliances, the bite plates are used (10 and 11) (as illustrated in FIG. 11).

Thus, the device (1) works by distributing the vibrating stimulus from the vibrating devices (5 and 6), through the vibrating straps (2) and from these to the orthodontic appliance (9) and/or teeth (92), respectively, through the clips (3) or bite plates (10 and 11).

When the clips (3) are used associated with vestibular orthodontic appliance (9), which can be moved along the vibrating strap (2), they are fastened by pressure to the orthodontic arch (91) that passes through the inside of the brackets (93) fixed to teeth (92). The vibrating devices (5 and 6), represented herein by groups of three, are activated alone or together, each one is activated by means of a dedicated on/off switch (4). The vibration is then transmitted by the strap (2) to clips (12) or (3), and then, directly to teeth (92) or through the orthodontic arch (91) attached to the brackets (93), respectively, thus beginning the therapeutic action. The device remains switched on according to the desired activation protocol for the specific case.

In the use of the device (1) associated with the lingual orthodontic appliance, the bite plates (10 and 11), already fixed to the vibrating strap (2) of the device (1) by clips (12) are positioned between the arcades after being adapted by pressure and light heating, in order to fit to teeth geometry (92). The vibrating force is directed to the teeth (92) by pressure of these against the bite plates (10 and 11), during the time stipulated by current protocol.

The vibrating device (1) further comprises at least one sensor (not shown) with vibrating devices (5 and 6), wherein said sensor is able to capture a plurality of parameters from inside the oral cavity and transmit such data remotely or via cable for further analysis.

The various parameters captured by sensors include, among others: oral pH, temperature and presence of ketone bodies.

The person skilled in the art will readily realize, from the description and the drawings shown, many equivalent forms of carrying out the invention to achieve the same result, in which case they are covered by the attached claims.

The invention claimed is:

1. A vibrating orthodontic device to be coupled to an arch of an orthodontic appliance, comprising:
   a plurality of vibrating devices arranged on a vibrating strap and a plurality of clips coupled to said strap in a sliding manner;
   the vibrating devices each comprise at least one battery, a micro vibrator and an actuating element all connected in order to enable the device as a whole to vibrate when turned on;
   said strap having an external surface coupled to the vibrating devices and said strap having internal surface facing the dental arch, the internal surface being equipped with a track having a "C" shaped cross-section with longitudinal tabs towards a central traversal axis (H-H) to provide two housings;
   the clips comprise first end which has upper and lower wings that stay in the housings of the track to couple the clips to the track, and a second end opposite from the first end of the clip that comprises a slit that enlarges towards the first end, forming a tear-drop-shaped cross-section opening, said slit dividing the clip into two tabs that fasten the apparatus to said arch.

2. The vibrating orthodontic device, according to claim 1, wherein the vibrating devices are three equally spaced on the strap, one on the front and two on the back positioned bear the end of the strap.

3. The vibrating orthodontic device, according to claim 1, wherein the plurality of vibrating devices includes a front device that has front slits partially dividing it into three segments, and two back devices have each have a unitary body.

4. The vibrating orthodontic device, according to claim 1, wherein the actuating element is chosen among a switch or a remote actuating component that can receive any type of actuating signal.

5. The vibrating orthodontic device, according to claim 1, further comprising a sensor associated with one of the vibrating devices, said sensors being capable of capturing parameters chosen among oral pH, temperature, presence of ketone bodies and or transmitting such parameters remotely or via cable.

6. A vibrating orthodontic device to be adapted to teeth by occlusion, comprising:
   vibrating devices arranged on a vibrating strap, a plurality of clips coupled to said strap in a sliding manner and bite plates integrated with the clips;
   said vibrating devices each comprising at least one battery, a micro vibrator and an actuating element, all connected together in order to enable the vibrating device as a whole to vibrate when turned on;
   said strap having an external surface coupled to vibrating devices and having an internal surface facing the dental arch, the internal surface having a track where the clips are coupled; the track having a "C" shaped cross-section with longitudinal tabs facing towards a central transversal axis (H-H), in order to provide two housings;
   each of the clips comprise a first end that has upper and lower wings that retain the clips inside the housings to couple the clips to the track and a second end opposite from the first end; and the bite plates are integrated with the clips on the second end of the clips.

7. The vibrating orthodontic device, according to claim 6, wherein the vibrating devices are three equally spaced on the strap, one on the front and two on the back positioned near the end of the strap.

8. The vibrating orthodontic device, according to claim 6, wherein the vibrating devices include a front device has front slits partially dividing it into three segments, and two back devices that each have a unitary body.

9. The vibrating orthodontic device, according to claim 6, wherein the actuating element is chosen among a switch or a remote actuating component that can receive any type of actuating signal.

10. The vibrating orthodontic device, according to claim 6, wherein the bite plates have two different sizes, two minor front bite plates at a front portion of the strap and two larger bite back bite plates in the back portion of the strap.

11. The vibrating orthodontic device, according to claim 10, wherein the front bite plates have uniform thickness and are thicker than the back bite plates; and the back bite plates have variable thickness, being thinner in a back portion of the back bite plate than in a front portion of the back bite plate.

12. The vibrating orthodontic device, according to claim 6, further comprising a sensor associated with one of the vibrating devices, said sensors being capable of capturing parameters chose among oral pH, temperature, presence of ketone bodies and of transmitting such parameters remotely or via cable.

\* \* \* \* \*